United States Patent
Kurashima

[19]
[11] Patent Number: 6,033,455
[45] Date of Patent: Mar. 7, 2000

[54] REPEATEDLY USABLE FILTER FRAME AND FILTER FOR FLUID USING THE SAME

[75] Inventor: Daisuke Kurashima, Tokyo, Japan

[73] Assignee: 3M Innovative Properties Company, St. Paul, Minn.

[21] Appl. No.: 09/106,229

[22] Filed: Jun. 29, 1998

[51] Int. Cl.[7] .................................................. B01D 25/04
[52] U.S. Cl. ................... 55/497; 55/502; 55/503; 55/506; 55/509; 210/445; 210/446; 210/450
[58] Field of Search ............................ 55/497, 502, 503, 55/506, 509; 210/445, 446, 450

[56] References Cited

U.S. PATENT DOCUMENTS

| Re. 32,171 | 6/1986 | van Turnhout . | |
|---|---|---|---|
| 3,932,153 | 1/1976 | Byrns . | |
| 4,148,732 | 4/1979 | Burrow et al. | 55/503 |
| 4,215,682 | 8/1980 | Kubik et al. . | |
| 4,826,598 | 5/1989 | Cain | 55/503 |
| 4,874,513 | 10/1989 | Chakraborty et al. | 55/503 |
| 5,108,709 | 4/1992 | Bugar et al. | 55/503 |
| 5,273,563 | 12/1993 | Pasch et al. | 55/503 |
| 5,468,384 | 11/1995 | Garcera et al. | 55/502 |
| 5,605,554 | 2/1997 | Kennedy | 55/503 |
| 5,720,790 | 2/1998 | Kometani et al. | 55/502 |

FOREIGN PATENT DOCUMENTS 0 265 163 A2   4/1988   European Pat. Off. .

OTHER PUBLICATIONS

KOKYO "Effectiveness of Filter for Spirography in Inspecting Lung Function", vol. 14, No. 6, pp. 641–645, 1955, Nishimura et al.

*Primary Examiner*—David A. Simmons
*Assistant Examiner*—Minh-Chau T. Pham
*Attorney, Agent, or Firm*—Gary L. Griswold; Robert W. Sprague; William J. Bond

[57] ABSTRACT

To provide a filter frame which enables a filtering medium to be easily renewed on a site and makes it possible to provide a filter at a low cost.

The filter frame comprises a pair of frame elements capable of being integrally coupled together through flange bonding, each frame element comprising a passage portion allowing the passage of a fluid to be filtered and a flange portion outwardly disposed at a peripheral end portion of said passage portion, and that each of said flange portions has at least one bending portion, and said two flange portions, when coupled together, are engaged with each other based upon at least one tongue-in-groove connecting portion with said filtering medium being sandwiched between said flange portions.

9 Claims, 3 Drawing Sheets

REPEATEDLY USABLE FILTER FRAME AND FILTER FOR FLUID USING THE SAME

TECHNICAL FIELD TO WHICH THE INVENTION BELONGS

The present invention relates to filtering fluids and, particularly, gases. More specifically, the invention relates to a filter frame for mounting and fixing a filtering medium for filtering fluid, and to a filter for filtering fluid by using such a filter frame. The filter frame, according to the present invention, can be easily assembled on a site to use it as a filter and can further be easily split for renewing filtering medium and can be assembled again. The filter of the present invention can be used for filtering a variety of fluids and, particularly advantageously, for filtering human breath in medical measuring apparatuses such as artificial respiratory machine, anesthetic machine, machine for measuring function of lung, spirometer, etc.

BACKGROUND OF THE INVENTION

Filters of a variety of types have heretofore been proposed for filtering fluids. Filters are known which comprise a housing for permitting the passage of fluid and a filtering medium mounted in the housing. The housing is air-tight so that no fluid leaks during the use, and is made unitary by ultrasonic melt-adhesion or like methods.

U.S. Pat. No. 3,932,153 discloses a filter which is effective in controlling, particularly, bacteria. As shown in cross section of FIG. 6, the filter 20 comprises a combination of a pair of conical flow path members 21 and 31 with flanges 22 and 32. The flanges which are joined together to form a housing and a flow path 23 is formed in the housing to permit the passage of fluid. The fluid flows as indicated by arrows. The flanges 22 and 32 are bonded together by ultrasonic melt-adhesion with a filtering medium 24 sandwiched therebetween, forming an air-tight housing. In order that the flanges of the filter can be easily positioned at the time of bonding while stretching the filter medium, one flange is provided with a V-shaped groove 25 and a concave groove 26 and the other flange is provided with a corresponding triangular projection and a convex projection. A similar filter has also been disclosed in European Patent Application Laid-Open No. 0.265,163.

In the journal KOKYU, "Effectiveness of a Filter for Spirography in Inspecting Lung Function", Vol. 14, No. 6, PP. 641–645, 1995, Nishimura et al. teaches the effectiveness of using a filter for spirography in an apparatus for measuring lung function. This is because, when the human breath is directly introduced into a measuring apparatus, bacteria contained in the breath, saliva and sputum enter into the circuitry in the apparatus, adversely affecting measurements. Or, when the apparatus is used repetitively, the human body may be infected with contaminated substances in the apparatus. The filter for spirography used in this apparatus is a special filter, C-8F (part number), manufactured by Chest MI Co., and its use is shown in FIG. 1 on page 642 of the journal KOKYU. Though not described in detail in the KOKYU, this filter is made of a plastic material and contains a pleated mesh-like filtering medium to enhance filtering efficiency. The housing of this filter is fabricated relying on ultrasonic melt adhesion.

When used for the medical measuring apparatuses such as artificial respiratory machines, anesthetic machines, machines for measuring function of lung, spirometers, etc., the above mentioned filter and other conventional filters are effective in removing bacteria, saliva and sputum from the human breath, making it possible to prevent the apparatuses from being contaminated with bacteria. Or, when the apparatuses are contaminated, on the other hand, such filters make it possible to prevent the human body from being infected with bacteria.

However, the above conventional filters are cumbersome to produce and are costly since the housing is formed into a unitary structure by ultrasonic melt adhesion or the like. According to the above-mentioned KOKYU, a disposable mouth piece that is discarded after each use costs 20 yen per piece, whereas a filter costs 290 yen per piece. Besides, since the filtering medium is firmly secured, the filter body, too, must be discarded when the filtering medium is contaminated, which is not economical. In particular, when the user of the filter is an infected patient, the filter must be discarded even though the filter body has not been contaminated, which is disadvantageous.

The object of the present invention is to provide a filter frame which can be repetitively used and can be easily manufactured being free from the above-mentioned inherent problems.

Another object of the present invention is to provide a filter for filtering fluid which is cheaply obtained and can be repetitively used upon renewing the filtering medium.

A further object of the present invention is to provide a filter which permits the filtering medium to be easily renewed on site where it is used even by a person who is not skilled at renewing filtering medium.

Other objects of the present invention will be easily understood from the following detailed description of the invention.

DESCRIPTION OF THE INVENTION

According to the present invention, there is provided a filter frame for mounting and fixing a filtering medium which can be repetitively used. The filter frame comprises a pair of frame elements capable of being integrally coupled together through flange bonding. Each frame element comprising a passage portion allowing the passage of a fluid to be filtered and a flange portion outwardly disposed at a peripheral end portion of said passage portion. Each of said flange portions has at least one bending portion, and said two flange portions, when coupled together, are engaged with each other based upon at least one tongue-in-groove connecting portion with said filtering medium being sandwiched between said flange portions. Here, as described below in detail, the words "tongue-in-groove connecting portion" appearing in the specification stand for means for engaging together the opposing flange portions of a pair of frame elements, such as a projection of one flange portion fitted into a recessed portion of another flange portion to engage them together, combination of a semispherical projection with a semispherical depression, a triangular projection fitted to a V-groove corresponding thereto, a waved projection fitted to a waved depression corresponding thereto, etc.

According to the present invention, there is further provided a filter for filtering fluid by comprising a filter frame of the present invention and a filtering medium which is sandwiched and secured between the flange portions of said filter frame.

According to the filter, of the present invention, a filter is completed by the at least one tongue-in-groove connecting portion and at least one bending portion formed in the flange portion of the frame member without requiring any further processing such as ultrasonic melt-adhesion. The filtering medium can be removably secured to the filter with the filtering medium being allowed to be renewed as required. The flange portion is provided with at least one bending portion, with the fluid flowing through the filter being prevented by the bending portion from flowing out through a gap between the flanges. The combination of the bending portion with the tongue-in-groove connecting portion makes it possible to increase the engaging force of the flange portions. The flange portions can be easily disengaged from each other by hand when the filter is not in use such as when the filtering medium is to be renewed.

The term "flange bonding" used herein is intended to mean the bonding or coupling mechanism which is substantially the same as that of "flange bonding" frequently used in the field of mechanical engineering. The bonding mechanism includes using a pair of frame elements that form the filter frame and also act as a flange. The opposed surfaces of said two frame elements are contacted with each other to form a filter frame. Note that in the flange bonding of the present invention, bolts or other securing means generally used in conventional flange bonding are not used, however, as will be described hereinafter, a tongue-in-groove connecting portion is included in the flange portion for fitting purposes in place of said means.

As described above, the filter frame of the present invention works to mount and secure the fluid filtering medium. Here, the word "fluid" includes a wide range of gases from gases for industrial use, through oxygen for therapy, up to human breath, and no limitation is imposed on the fluid so far as it is to be filtered. Therefore, the filter frame of the present invention and the filter using the filter frame can be advantageously used for filtering devices for a variety of industrial and personal uses, as well as for medical measuring apparatuses. For easy comprehension of the invention in the following description, the fluid (that is to be filtered) exemplified is human breath.

According to the present invention, the filter frame comprises a pair of frame elements which can be coupled together as a unitary structure through flange bonding of the corresponding flange portions of the frame elements. The frame elements can be coupled without additional fastening means as adhesive or as ultrasonic melt-adhesion. The two frame elements are secured together as a unitary structure based on a particular engaging structure of the flange portions.

The frame elements each have a passage portion through which the fluid to be filtered flows and a flange portion which faces outwards on a peripheral end portion of the passage portion. There is no particular limitation in the shape of the passage portion so far as the flowing path ensures a smooth flow of the fluid to be filtered. Desirably, the passage portion has a cylindrical or similar shape. Also from the standpoint of firmly holding and tensioning the filter medium by the flange portions is desired that the flow path has a circular, oval or polygonal cross-sectional shape. In order that tensioning stress is uniformly dispersed in the flange portions is desired that the flow path has a circular or oval cross-sectional shape. It is further desired that the filter is as small as possible for its intended use.

The flange portion of each frame element has at least one bending portion in combination with at least one tongue-in-groove connecting portion. When the two opposing frame elements are coupled together via the flange portions, a strong engagement is accomplished by the fitting action of both the bending portion and the tongue-in-groove connecting portion were in addition, the filtering medium is sandwiched between the flanges and firmly held. The filtering medium sandwiched between the flange portions can extend into the gap between the flange portions up to any desired position based upon the desired fastening effect for fastening. For instance, the filtering medium can extend in front of a bending portion of the flange portion or beyond a bending portion. As required, the filtering medium may be extended up to a position in front of the tongue-in-groove connecting position. To more strongly hold the filtering medium, the flange portion may be additionally provided with a tongue-in-groove structure which is different from that used in fitting of the flange portions, such as a concave convex shape, senispherical shape, wave shape, U-shape, V-shape or arcuate shape, for example, the V-shaped connecting portion 29 in FIG. 5 which will be referred to hereinafter.

The tongue-in-groove connecting portion formed in the flange portion may be of any form and may be disposed at any position. Concerning the tongue-in-groove connecting portion, for example, one flange portion may be provided with a concave depression and the other flange portion may be provided with a convex projection. As will be described with reference to the drawings in the chapter of embodiments, furthermore, one flange portion may be provided with a semispherical depression and the other flange portion may be provided with a semispherical projection. Moreover, the tongue-in-groove connecting portion may have a wave shape, U-shape or arcuate shape in cross section when further increased engaging strength is required, it is recommended to fold the flange portion three times to provide three bending portions therein and dispose the tongue-in-groove connecting portion substantially adjacent to one of the bending portions on a peripheral end portion of the flange. Though the illustrated embodiment illustrates only one tongue-in-groove connecting portion, there may be provided a plurality of tongue-in-groove connecting portions as required.

The frame elements can be made of various materials, but are preferably a flexible plastic material. Examples of the preferred plastic material may include general-purpose thermoplastic materials such as polypropylene, polyethylene and polystyrene, to which, however, the invention is in no way limited. By using these plastic materials as starting materials, the frame elements can be molded in a desired shape relying upon an ordinary molding method such as injection molding, vacuum molding or compressed-air molding.

The size of the frame element can be widely changed depending upon such factors as the size of a desired filter. For example, when the filter is to be used for filtering human breath in a medical measuring apparatus, it is desired that the frame element is small enough so that the user does not find it cumbersome to use. Similarly, it is desired that the frame element thickness is as small as possible to reduce the weight but still provide a desired strength to the filter.

The filtering medium can be easily secured by engaging the flange portions of the filter frame together as described above. There is no particular limitation on the filtering medium provided it exhibits filtering ability required for the filter, and has a thickness and strength such that can be held between the flange portions. Therefore, the filtering medium suited for the filter of the present invention may be selected from a variety of commercially available filter media. It is generally recommended to use a filtering medium of a nonwoven fabric made of a natural or synthetic material. When the fluid to be filtered is the human breath, it is desired to use a nonwoven electret filtering medium having a low pressure loss and a high trapping efficiency to have low permeation resistance at the time of spontaneous or forced respiration yet highly efficient trapping of bacteria, sputum, etc. A nonwoven electret filtering media disclosed in Japanese Examined Patent Publications (Kokoku) Nos. 56-47299 and 59-124, and commercially available as "FILTRETE", from Sumitomo 3M Company are acceptable. When "FILTRETE" is used, it is desired that its basis weight be from about 10 to about 300 g/m$^2$. When a hygroscopic function is required, the filtering medium may be laminated with a hygroscopic layer comprising a nonwoven impregnated with a hygroscopic agent or it may contain a hygroscopic agent dispersed therein. Similarly, if desired, the filtering medium may be laminated with other layers such as a deodorant layer or antibacterial layer. For example, a nonwoven could be impregnated with a deodorant or antibacterial agent, or it may contain any additive dispersed therein, for example, a deodorant, antibacterial agent or the like. Further, the filtering medium may be either a single layer structure or multi-layer structure.

According to the present invention, the complete filter can be obtained by using the filter frame according to various procedures. For instance, a filtering medium of a size equal to, or larger than, the flange portion is brought into contact with the flange portion of one frame element of the filter frame. Then, while stretching the filtering medium, another frame element is pushed onto the frame element on which the filtering medium has been brought into contact, and the two frame elements are engaged together via the tongue-in-groove connecting portions and bending portions of the flange portions. There is thus formed a filter frame bonded together as a unitary structure, and a filtering medium is secured in the frame maintaining air-tightness in the flow path of the fluid.

After used a predetermined number of times, the filter can be easily split in order to replace the filtering medium that is contaminated or damaged by a new filtering medium. Basically, the filter is split in the opposite order used in assembling the filter. That is, the end of the outer flange portion between the two flange portions is peeled outward by a finger tip. Then, the stable engagement loses balance, and the filter is easily split. When the interior of the filter frame has been contaminated, or may have been contaminated with bacteria and the like, it is recommended to sterilize or pasteurize the filter frame by a suitable sterilizing means such as an ethylene oxide (EO) sterilizing device or boiling device, or to wash the filter frame with a suitable washing agent.

The filter of the present invention can be advantageously used in a variety of filtering devices or in similar devices. When the filter of the present invention is used for an intake/exhaust cylinder of a spirometer or an apparatus for measuring the function of a lung, no particular machining needs be effected to form the fluid inlet and outlet ports of the filter frame. What is needed is that the fluid outlet has a diameter that is suited for fitting to the insertion end of the intake/exhaust cylinder, so that the fluid outlet of the filter frame is fitted to the insertion end of the intake/exhaust cylinder. The fluid inlet of the filter frame may have its own form or may be so designed so that a disposable mouth piece can be attached thereto, so that it can be used by unspecified number of persons. Or, the fluid inlet of the filter frame may be threaded or may be provided with a flange, a swollen portion or a recessed portion so that other member can be connected thereto as required.

DETAILED DESCRIPTION OF THE PREFERRED EMBODIMENTS

The filter frame and the filter according to a preferred embodiments of the present invention will now be described in detail with reference to the accompanying drawings. Here, however, it should be understood that the present invention is in no way limited to these embodiments only.

Figure 1:
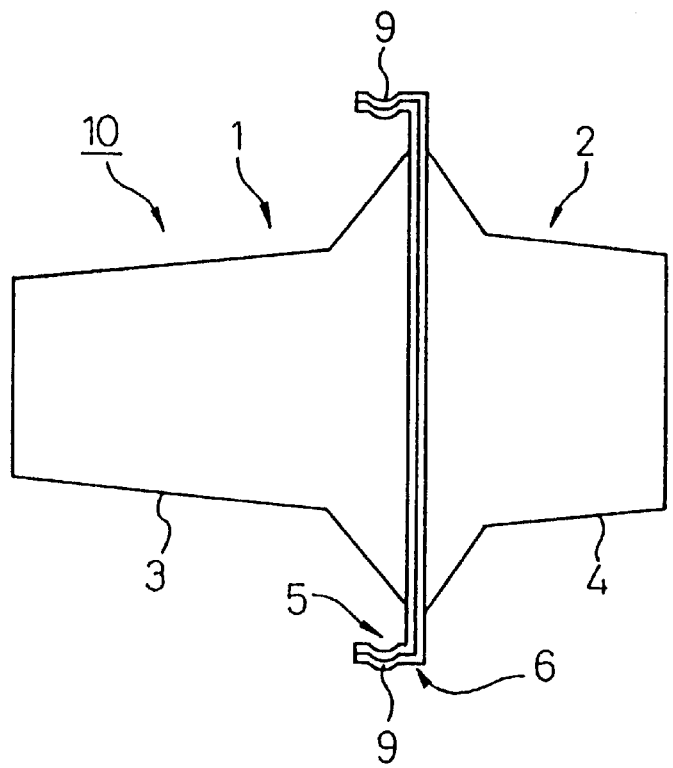
FIG. 1 is a front view illustrating a preferred filter for filtering the breath assembled by using a filter frame of the present invention.
Figure 2:
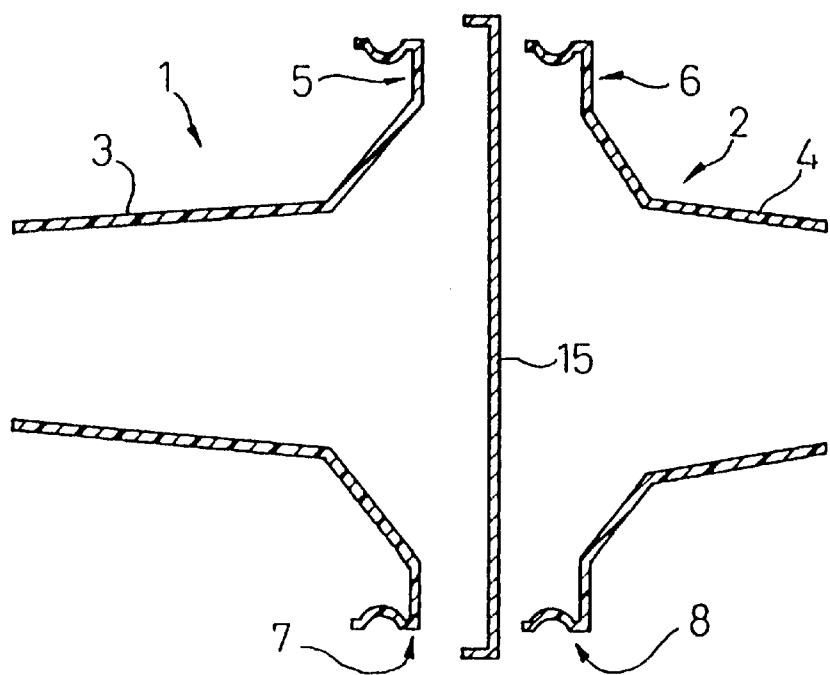
FIG. 2 is a sectional view illustrating in an expanded manner the constitution of the film shown in FIG. 1.

FIG. 1 illustrates a preferred filter for filtering breath assembled by using the filter frame according to the present invention. The filter frame element will be described with reference to FIGS. 2 and 3. The filter 10 has a filter frame comprising a pair of frame elements 1 and 2 that are coupled together as a unitary structure via flange portions 5 and 6. In this filter, the frame elements 1 and 2 are provided at their major portions with passage portions 3 and 4 to permit the passage of breath. Flange portions 5 and 6 have bending portions 7 and 8 (see FIG. 2), respectively. The flange portions can be firmly engaged together due to the bending portions and the neighboring tongue-in-groove connecting portions 9, so that air-tightness is maintained in the housing. As shown in FIG. 2, the filtering medium 15 is disposed at the center of the passage portions 3 and 4 in a manner to interrupt the flow path formed by the passage portions, and is secured by the engagement of the flange portions 5 and 6. The filtering medium 15 is disposed in a stretched manner in the filter 10 nearly perpendicular to the flow direction of the breath.

Figure 3:
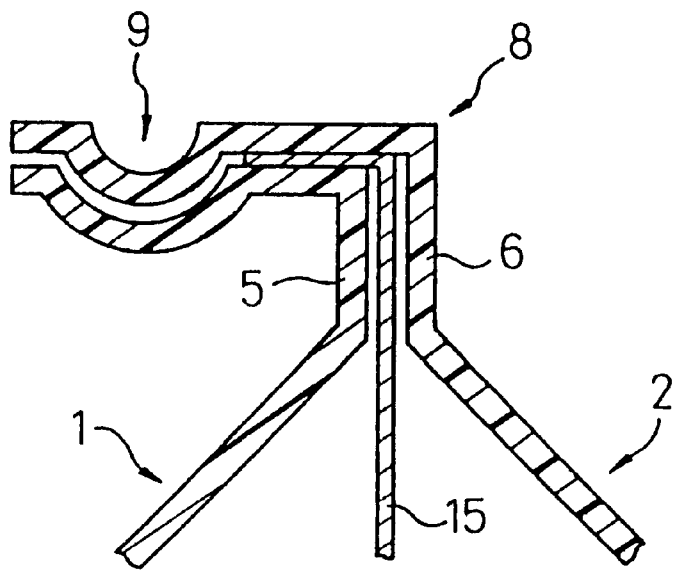
FIG. 3 is a sectional view illustrating on an enlarged scale the constitution of the flange portions of the filter shown in FIG. 1.

The engaging state of the flange portions of the filter 10 shown in FIGS. 1 and 2 will become more obvious from the enlarged sectional view in FIG. 3. In the diagrammed embodiment, the tongue-in-groove connecting portion 9 is formed by the combination of a semispherical depression and a corresponding semispherical projection. As described earlier, however, the tongue-in-groove connection portion 9 may have any other structure such as a concave/convex structure, a waved structure or the like. The filtering medium 15 extends to a position in front the tongue-in-groove connecting portion 9 in a gap formed by the flange portions 5 and 6. If sufficient securing is obtained, however, the filtering medium 15 may terminate at the bending portion or at a portion in front thereof.

Figure 4:
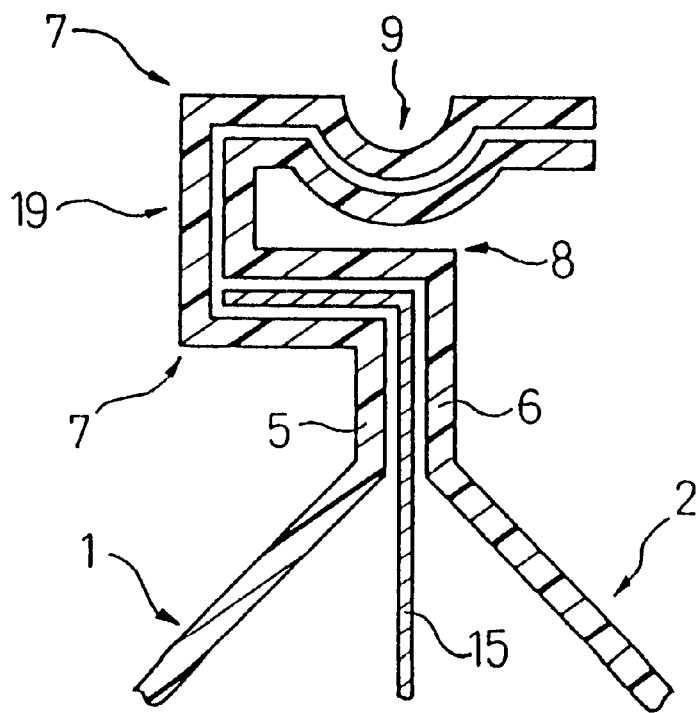
FIG. 4 is a sectional view illustrating, on an enlarged scale, another preferred embodiment of the filter for filtering the breath assembled by using the filter frame of the present invention and corresponds to FIG. 3.

FIG. 4 is a modified embodiment of the filter shown in FIG. 3. In this modified embodiment, the number of the bending portions 7 and 8 are increased from one to three, and the tongue-in-groove connecting portion 9 is formed in an end portion of the flange portions 5 and 6. In this embodiment, a tongue-in-grove connecting portion 19 of a concave/convex structure is additionally formed by the three bending portions in addition to the tongue-in-groove connecting portion 9. When the flange portions are bent three times as shown, the entire flange portion produces elasticity. Due to the internal pressure produced in the flow passage when the filter is being used, stress is produced so as to expand the filter frame, whereby the engaging portions of the flange portions are more strongly about each other. Furthermore, the end of the flange extending beyond the engaging portion and located above the surface for holding the filtering medium, can be utilized as a guide for inserting the frame element at the time when the opposing frame elements of the filter frame are engaged.

Figure 5:
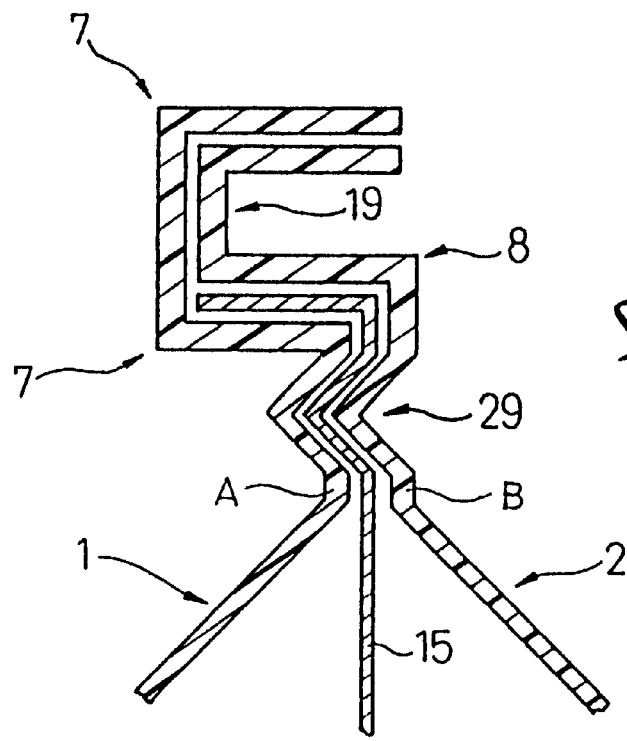
FIG. 5 is a sectional view illustrating, on an enlarged scale, a further preferred embodiment of the filter for filtering the breath assembled by using the filter frame of the present invention and corresponds to FIG. 3.
Figure 6:
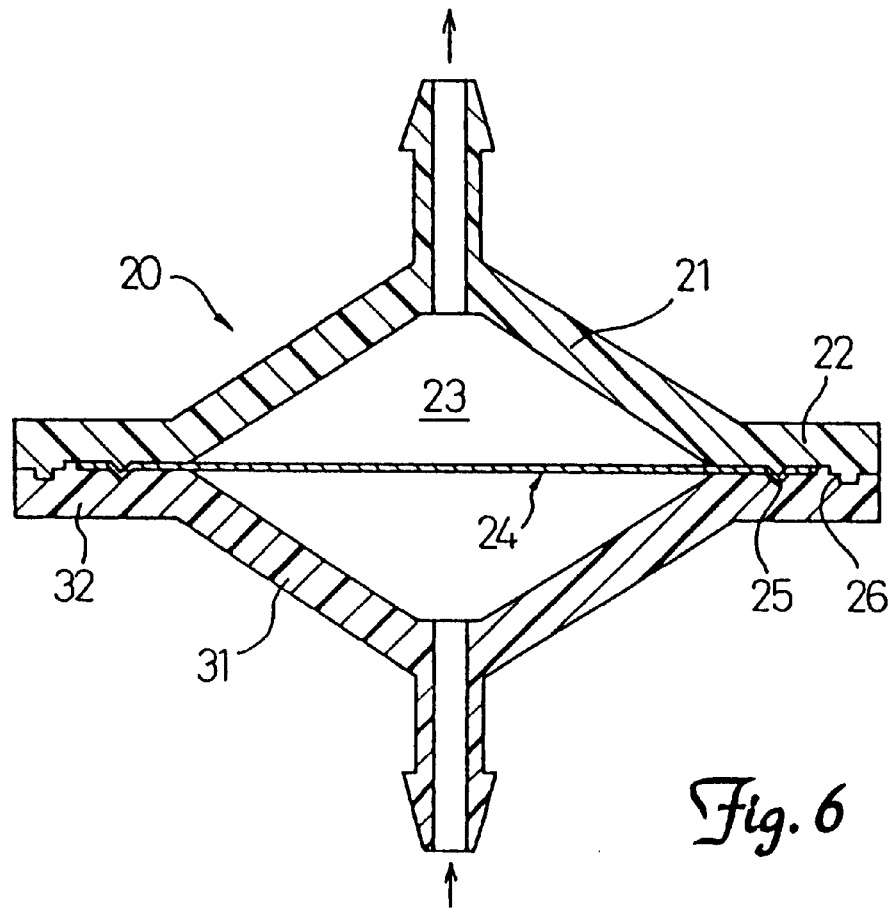
FIG. 6 is a sectional view illustrating a conventional filter for filtering the breath.

FIG. 5 illustrates a modified embodiment of the flange bonding portion shown in FIG. 4. In this diagrammed embodiment, the flange portions 5 and 6 are engaged together by the tongue-in-groove connecting portion 19 formed by the three bending portions of the concave/convex structure, and the tongue-in-groove connecting portion 9 shown in FIG. 4 is eliminated. In this case, an additional V-shaped tongue-in-groove connecting portion 29 is provided at a position closer to base portions A and B of the flanges to reinforce holding of the filtering medium 15 and to stretch the filtering medium 15.

Described below is the fabrication of the filter according to the present invention along with characteristics of the filter. The filter fabricated is the type described with reference to FIG. 1 having the flange portion as illustrated in FIG. 4.

Filter frame elements were obtained by vacuum-molding a polystyrene sheet (0.7 mm thick). The filtering medium was sandwiched and secured between the opposed flange portions of the filter frame elements to complete the filter of the present invention. The filtering medium used was Filtrete™ GSB-20 DSCC-A (about 0.7 mm thick, weight of about 50 g/m²), commercially available from Sumitomo 3M Co.

The obtained filter was tested for air-tightness using a testing apparatus. The pressure inside the filter was raised to 500 mmAQ, and soapy water was applied to the outer peripheries of the engaged portion of the flange portions. No bubbles were seen from the soapy water applied, indicating that no air was leaking from the filter. Air was also blown through the filter at a rate of 2000 liters a minute with no peeling of filtering medium.

According to the present invention as described above, there is provided a filter frame which is simple in structure and can be produced easily and at a reduced cost. The filter frame can be split into filter frame elements that can be placed upon other requiring reduced space for transportation and storage of the filter frame. Furthermore, the filter can be easily assembled on site where the filter is to be used, without any particular skill needed. Furthermore, the filter can be easily split apart. Therefore, the filtering medium can be used repetitively when the filter medium is contaminated or damaged and replaced by a new filtering medium. Prior to replacing the filtering medium, the used filter frame can be easily washed or sterilized. Reuse of the filter frame saves resources and reduces the amounts of waste. Also, since the filters can be fabricated without requiring high frequency melt-adhesion, reduction in the number of manufacturing steps is achieved as well as cost reduction.

We claim:

1. A reusable filter frame for mounting and fixing a filtering medium, comprising a filter frame which comprises a pair of frame elements capable of being integrally bonded together through flange bonding, each frame element comprising a passage portion allowing the passage of a fluid to be filtered and a flange portion, having an inside face and an outside face, outwardly disposed at a peripheral end portion of said passage portion, each of said frame elements flange portions have at least one bending portion, which bending portions bend in opposite directions on the opposing frame elements, said two frame element flange portions engage such that an outside face of one flange portion and an inside face of the other flange portion substantially continuously engage with each other with at least one tongue-in-groove connecting portion, along with sandwich$_{13}$ wise securing of said filtering medium between at least a portion of the two engaged flange portions.

2. A filter frame according to claim 1, in which said tongue-in-groove connecting portion is constituted from a combination of a semispherical projection formed on one flange portion and a semispherical depression formed on another flange portion.

3. A filter frame according to claim 1, in which said flange portion has one bending portion, and said tongue in-groove connecting portion is disposed substantially adjacent to said bending portion on a peripheral end portion of the flange.

4. A filter frame according to claim 1, in which said flange portion has three bending portions, said tongue in-groove connecting portion is disposed substantially adjacent to one of said bending portions on a peripheral end portion of the flange.

5. A filter frame according to claim 1, in which said tongue-in-groove connecting portion is constituted by a combination of a convex projection formed by three bending portions on one flange portion, and a concave depression formed by three bending portions on another flange portion.

6. A filter frame according to claim 5, in which said filter frame is formed from a flexible plastic material.

7. A filter for filtering fluid comprising a filter frame as defined in claim 6 and a filtering medium which is sandwiched and secured with flange portions of said filter frame.

8. A filter according to claim 7, in which said filtering medium is a nonwoven electret filtering material.

9. A filter according to claim 8, which is used for filtering human breath.

* * * * *

UNITED STATES PATENT AND TRADEMARK OFFICE
CERTIFICATE OF CORRECTION

PATENT NO. : 6,033,455  
DATED : March 7, 2000  
INVENTOR(S) : Daisuke Kurashima Page 1 of 1

It is certified that error appears in the above-identified patent and that said Letters Patent is hereby corrected as shown below:

Column 4,  
Line 13, "senispherical" should read -- "semispherical" --.

Column 8,  
Line 22, delete the subscript -- $_{13}$ -- after "sandwich".

Signed and Sealed this

Fifth Day of March, 2002

*Attest:*

JAMES E. ROGAN  
*Attesting Officer*     *Director of the United States Patent and Trademark Office*